United States Patent [19]

Day et al.

[11] Patent Number: 5,728,323
[45] Date of Patent: Mar. 17, 1998

[54] PROCESS FOR PREPARING DIALKYL TETRAHALOPHTHALATES

[75] Inventors: James F. Day, Greensboro; James J. Good, Archdale, both of N.C.

[73] Assignee: Unitex Chemical Corporation, Greensboro, N.C.

[21] Appl. No.: 554,262

[22] Filed: Nov. 6, 1995

[51] Int. Cl.$^6$ .................... C09K 21/00; C07C 67/00; C07C 69/00
[52] U.S. Cl. .................... 252/601; 252/601; 560/62; 560/65; 560/78; 560/99
[58] Field of Search .................... 252/601; 560/99, 560/78, 62, 65

[56] References Cited

U.S. PATENT DOCUMENTS

| | | | |
|---|---|---|---|
| 2,780,643 | 2/1957 | Buchner | 560/99 |
| 2,805,246 | 9/1957 | Bourguignon et al. | 260/475 |
| 2,862,958 | 12/1958 | Goreau | 260/475 |
| 3,293,282 | 12/1966 | Farrar et al. | 260/475 |
| 4,105,710 | 8/1978 | Thomas et al. | 260/869 |
| 4,227,010 | 10/1980 | Hood | 560/77 |
| 4,277,379 | 7/1981 | Hermann et al. | 252/608 |
| 4,284,793 | 8/1981 | Sagara et al. | 560/78 |
| 4,304,925 | 12/1981 | Watanabe et al. | 560/78 |
| 4,376,837 | 3/1983 | Jenkner et al. | 524/108 |
| 4,394,471 | 7/1983 | Keogh | 524/92 |
| 4,552,911 | 11/1985 | Cohnen et al. | 524/94 |
| 4,659,381 | 4/1987 | Walters | 106/18.16 |
| 4,740,537 | 4/1988 | Silver | 523/200 |
| 4,754,053 | 6/1988 | Mamuzic et al. | 560/78 |
| 4,912,158 | 3/1990 | Bohen et al. | 524/288 |
| 5,036,121 | 7/1991 | Coaker et al. | 524/100 |
| 5,049,697 | 9/1991 | Bohen et al. | 560/83 |
| 5,114,786 | 5/1992 | Louis | 428/270 |
| 5,208,366 | 5/1993 | Bohen et al. | 560/83 |

FOREIGN PATENT DOCUMENTS

| | | | |
|---|---|---|---|
| 50-05701 | 3/1975 | Japan | C07C 69/80 |
| 6220264 | 8/1994 | Japan . | |
| WW8803542 | 5/1988 | WIPO . | |

OTHER PUBLICATIONS

Weissermel, Klaus and Hans–Jurgen, Arpe, Industrial Organic Chemistry, Second, Revised and Extended Edition, translated by Lindley, Charlet R., 1993; pp. 132–134, 206–208.

Primary Examiner—Sharon Gibson
Assistant Examiner—Deanna Baxam
Attorney, Agent, or Firm—Olive & Olive, P.A.

[57] ABSTRACT

A process for the preparation of dialkyl tetrahalophthalates. A tetrahalophthalic anhydride or acid is dissolved in excess $C_1$–$C_{18}$ alkanols. Residual sulfuric acid is removed by treatment with magnesium acetate or multiple water washes. The mass is esterified with a tetraalkyl titanate, and residual acidic components are removed by treatment with magnesium silicate. These treatments improve processability, production cycle time, product color, clarity and purity.

20 Claims, No Drawings

PROCESS FOR PREPARING DIALKYL TETRAHALOPHTHALATES

BACKGROUND OF THE INVENTION

1. Field of the Invention

This invention relates to improved methods for preparing dialkyl tetrahalophthalates which are used as flame retardants and/or processing aids.

2. Description of the Related Art

Tetrahalophthalates and related compounds are often used for flame retardants, as well as plasticizers in various applications. One example is in the formation of polymeric compositions used for forming primary insulation and protective jacketing for electrical conductors. Thus, Coaker et al. (U.S. Pat. No. 5,036,121) uses brominated phthalic acid esters together with polyvinyl chloride. These compounds may also be used for imparting enhanced flame resistance to wool (U.S. Pat. No. 4,277,379). The disclosures of these references and of the other publications and patents referred to herein are incorporated herein by reference.

The process for preparation of tetrahalophthalates as known in the art utilizes halophthalic anhydrides or acids. Typically, such an anhydride is made with concentrated $H_2SO_4$ and the elemental halide, resulting in a product which has substantial amounts of residual acid. Residual acidity in the halophthalic anhydride causes decarboxylation resulting in lower phthalate ester product purity and in poor color.

In addition, the process for the preparation of dialkyl tetrahalophthalates by reacting a tetrahalophthalic anhydride with an alkanol in the presence of a lower tetraalkyl titanate as is well known in the art, results in products that have high residual titanium, causing turbidity as well as poor insulative properties. Turbidity can be a problem if it makes the product less amenable to being colored, for example, in color coded wiring, or in various household items.

Numerous processes have been described for the preparation of dialkyl phthalates by esterification of various alcohols with phthalic anhydride or acid in the presence of acidic catalysts, such as sulfuric acid, phosphoric acid, toluene sulfonic acid, and methane sulfonic acid. The use of acidic catalysts with tetrahalophthalic anhydride or acid typically results in slow rates of esterification as well as poor product, color, quality, and yield, thus making these catalysis systems less suitable for commercial production.

Spatz et al. (I & EC Product Res. and Dev. 8:391, 1969) discloses the preparation of di-2-ethylhexyl tetrabromophthalate using phosphoric acid catalysis. In this process, product yield is poor with significant decarboxylation of the intermediate monoester.

Nomura et al. (published Japanese Patent Application No. 50-05701, 1975) describes the use of tetraalkyl titanates in the presence of alkali metal salt to prepare dialkyl tetrabromophthalates; however, this process does not deliver the ultra-low acid values (less than 0.01 meq/100 gram sample) as required by current industry standards.

Sagara et al. (U.S. Pat. No. 4,284,793) discloses a method for producing plasticizers with low residual titanium, in which phthalic anhydride is reacted with an alcohol in the presence of a titanate catalyst. The resultant ester is treated with a solid alkali, such as sodium carbonate, and adsorbing agent(s) in the absence of water. Treatment with this methodology results in an unfilterable tetrabromophthalate.

Watanable et al. (U.S. Pat. No. 4,304,925) discloses a process for purifying esters, such as those formed from phthalic anhydride and ethyl hexyl alcohol, when organotitanium compounds are used as catalysts, where water is added to the esterification mixture and the mixture is heated. The resultant tetrabromophthalate is unfilterable and esterification rates are very slow.

Mamuzic et al. (U.S. Pat. No. 4,754,053) discloses the preparation of tetrabromophthalate diesters using sodium carbonate decahydrate as an essential part of the process. While low acid values are achieved by use of the sodium carbonate decahydrate, product color is reported as gold and product purity as 92.9%. This patent does not report on product turbidity.

Bohen et al. (U.S. Pat. Nos. 5,049,697 and 5,208,366) disclosed a process for the preparation of dialkyl esters of polyhaloaromatic acids catalyzed by the use of various organometallic catalysts, such as organotitanates, as well as organo-tin, antimony and zirconium compounds. The products in these patents are described as yellow or dark oils.

Accordingly, the primary object of this invention is to prepare low color, high purity dialkyl tetrahalophthalates, which may be used as fire retardants, with ultra-low acid values. Products known in the art do not have both such a low acidity and such a low concentration of sodium, residual metals, and other color-causing components as the products of the invention.

Other objects and advantages will be more fully apparent from the following disclosure and appended claims.

SUMMARY OF THE INVENTION

The invention is an improved process for the preparation of dialkyl tetrahalophthalates. A tetrahalophthalic anhydride or acid is dissolved in an excess amount of $C_1$–$C_{18}$ of one or more alkanols. Residual sulfuric acid, not completely removed in prior methods, is removed by treatment with magnesium acetate or multiple water washes. Esterification with a tetraalkyl titanate catalyst is followed by removal of residual acidic components by treatment with a Group II alkali metal salt, such as magnesium silicate. These treatments improve processability, production cycle time, product color, clarity and purity.

Other aspects and features of the invention will be more fully apparent from the following disclosure and appended claims.

DETAILED DESCRIPTION OF THE INVENTION AND PREFERRED EMBODIMENTS THEREOF

The method of the invention for preparation of a dialkyl tetrahalophthalate utilizes a tetrahalophthalic compound selected from the group consisting of tetrahalophthalic anhydrides and tetrahalophthalic acids. Dihalo aromatic acids have a lower halogen proportion, and are generally known to be less effective as flame retardants. The tetrahalophthalic anhydride or acid used in this invention may be of tetrabromo- or tetrachloro-substitution on the aromatic ring, with tetrabromophthalic anhydride the preferred embodiment. Tetrahalophthalic compounds other than the tetrachloro- and tetrabromo- derivatives are not generally available. The tetrabromo- compound appears to have the best flame retardant capability. Also, the tetrachloro- compound is less widely available than the tetrabromocompound, and may present increased environmental risks. The tetrabromophthalic anhydride or acid is preferred in the invention. The anhydride is more easily available and therefore is the most preferred form.

In the invention, the tetrahalophathalic compound is reacted with an excess of alkanol, as is known in the art, to form a reaction mass. The alkanol is selected from $C_1$ to $C_{18}$ alkanols, or a mixture thereof. Alcohols with more carbons that are solid are not useful in the invention. The alkanol in this invention may be a $C_1$ to $C_{18}$ primary or secondary alkanol with linear or branched alkyl moieties. The preferred alkanols are 2-ethylhexanol and 3,3,5-trimethylhexanol, as well as mixtures of $C_8$ to $C_{15}$ alkanols resultant from Oxo- and Ziegler manufacturing processes as known in the art (see Weissermel, K. and Arpe, H-J., *Industrial Organic Chemistry*, pages 132–134, 206–208, VCH Publishers, New York, 1978).

Tetrahalophthalic anhydride may contain up to 0.30% residual sulfuric acid. Residual sulfuric acid resultant from the preparation of the original tetrahalophthalic anhydride is removed by serial hot water washing or preferably by the neutralization with a first Group II alkali metal salt, more preferably a Group II alkali metal salt of a lower carbon chain acid, and most preferably magnesium or calcium acetate. This treatment must be done before esterification to achieve low product color. If hot water is used (about 90° C.), typically 3–4, 300-ml aliquots of water (usually about 1 part water to 2 parts anhydride+alkanol) have been found to be sufficient to remove the residual sulfuric acid in the aqueous phase to less than 0.1%, when a mole of anhydride is using in the starting reaction mix. If less water is used, more washes are generally required to achieve the results of the invention. The water wash treatment, while being effective, is substantially more time-consuming than adding a Group II alkali metal salt, which is the preferred treatment.

Preferably treatment with a first Group II alkali metal salt is used instead of a water wash as the second step to remove acidity. A weak base is preferred, such as magnesium acetate, to neutralize the acid. Alternatively, calcium acetate may be used. While use of sodium acetate is possible to remove acidity, this treatment results in adding sodium ions in the product, which is generally not desired. Use of an acetate ensures that the pH will be less than 7.0 which is critical because the titanium catalyst is sensitive to, and is destroyed by, alkaline pH. The first Group II alkali metal salt is used at 0.01 to 10 percent of the weight of the reaction mass (defined as the weight of the original reactants, preferably at 0.1 to 0.5 weight percent, most preferably at stoichiometric levels equal to that of the residual sulfuric acid in the tetrahalophthalic anhydride. The removal of residual acidity introduced by the sulfuric acid is essential for good finished product color. The removal of residual acidity is also essential to allow higher esterification temperatures (180°–220° C.) which permits shortened esterification times without substantial decarboxylation of the intermediate monoester. Decarboxylation, if present, is a problem because it results in lower product purity.

The solution which has been water washed or treated with a first Group II alkali metal salt is dried by azeotroping out the water to a content of less than 0.05% by means known in the art. The primary reason for this step is the sensitivity to water of the catalyst used in the next step.

The product is then esterified with a neutral catalyst which may be an alkyl titanate catalyst or zirconium tetrabutoxide. An alkyl titanate catalyst is normally used in the industry. The esterification catalyst is a $C_1$ to $C_{18}$ tetraalkyl titanate, preferably a $C_8$ to $C_{18}$ tetraalkyl titanate, which most preferably is an alkyl identical to that of the alkanol esterified into the product, thereby limiting the preparation of mixed esters due to the transesterification of the alkyl groups of the catalyst into the product.

The esterification is carried out in an inert atmosphere, such as argon or nitrogen, at 160°–240° C., preferably at 190°–210° C. An azeotropic solvent or entrainer, such as a nonreactive aromatic or aliphatic hydrocarbon, for example, xylene or toluene as is known in the art, is added to shorten the esterification time. An inert carrier gas, such as argon, nitrogen, or carbon dioxide, may be used to drive off the reaction water formed during the esterification. The esterification is continued until residual acidity drops to less than 1.0 meq/100 gram sample, preferably less than 0.5 meq/100 gram sample at which time the excess alkanol is removed by vacuum distillation. This vacuum distillation decreases the residual acidity to less than 0.2 meq/100 gram sample. Excess alcohol must be removed to increase flash point and decrease volatility of the finished product.

In another important step of the invention, the residual acidity from the reaction is removed by the addition of 0.1 to 20 percent of a second Group II alkali metal salt, such as magnesium silicate (Magnesol® from the Dallas Group) or calcium silicate, plus an equal weight of water. This step is done after esterification; otherwise, the tetrahalo anhydride would be unnecessarily treated, which would consume raw material needlessly. Magnesium silicate makes the salts of titanium insoluble so that more of the turbidity-causing titanium drops out of the solution. Although magnesium or calcium oxide, or magnesium or calcium hydroxide, may be used at an equal weight percent basis as the magnesium silicate, there is a resultant decrease in filtration rates. Use of Group I alkalis, other than LiOH and lithium silicate is not desirable because of their alkalinity (loss of product yield with poor filtration), and some metal contamination ($Li^+$ and titanium) occurs with the lithium alkalis.

The addition of the water in the step discussed above is essential for the neutralization of the residual acidity by the magnesium silicate. Further, the water neutralizes the residual unreacted monoester intermediate. Water acts as a phase transfer agent. Magnesium silicate is a powder. The reaction conditions are 50°–95° C., preferably 90° C. for 1 to 4 hours after which the water of the neutralization is removed by vacuum distillation at 90°–140° C. This drying technique is essential to driving the neutralization to completion as well as the formation of a granular precipitant which is easily removed with conventional filtration methods, such as vacuum or pressure filtration.

The treatment with magnesium silicate decreases product color 1 to 5 Gardner color units (A.O.C.S. Method Td 12-64T) as compared to 5–15 Gardner color units. This treatment removes essentially all residual titanium, thus producing a haze-free product even at low temperatures. These Group II alkali metal silicates are particularly advantageous since filter aids, such as diatomaceous earth, are not required and the Group II alkali metal silicate adsorbs only small quantities of finished product, thereby improving product yield.

Products prepared according to the invention have a purity of 93–95.5%, with an average of 95–95.5%, whereas prior methodologies at their best have only reached a purity of about 93%, except for the Bowen process discussed above, which has high color levels.

The final product of the invention can be washed again with LiOH if it is desired to increase the product purity and assure the minimum level of acidity.

The Gardner color units of the final product are decreased to about 10 without the water wash or Mg acetate but with the magnesium silicate (as compared to about 15 without either treatment). The water wash or the magnesium acetate treatment plus the magnesium silicate treatment decreases the Gardner color units to about 1–2.

The features and advantages of the present invention will be more clearly understood by reference to the following examples, which are not to be construed as limiting the invention.

EXAMPLES

Example I

1. Tetrabromophthalic anhydride (464 grams), which typically contains 0.08–0.15% sulfuric acid, is dissolved in 2-ethylhexanol (390 grams) at 90° C. as is known in the art.
2. The solution is serially washed with aliquots of 300 grams of hot water at 90° C. until the residual sulfuric acid in the aqueous phase is less than 0.1%.
3. The solution is dried by azeotroping out water at 160°–190° C. until the water content is less than 0.05%.
4. The reaction mass is esterified at 195°–205° C. in a 1 liter reaction flask equipped with a Dean-Stark trap, with a catalytic quantity of tetra-2-ethylhexyl titanate (6 grams) until residual acid values are less than 0.5 meq/100 grams sample. The total esterification time is less than 6 hours.
5. The excess 2-ethylhexanol is distilled off under vacuum, further reducing the residual acidity to less than 0.2 meq/100 grams sample.
6. The reaction mass is cooled to 90° C. and treated with 7 grams magnesium silicate and 7 grams water, each of which is slurried into the reaction mass with mixing. The amount of water preferred is 1–2 times that of magnesium silicate (at 0.1 to 20 weight percent). The acid value is checked before filtration (next step) to be sure that it is low.
7. After treatment the reaction mass is dried under vacuum to less than 0.05% water and vacuum-filtered hot with a Buchner funnel as known in the art. The resulting product (692 grams) has the following properties:

Appearance: Clear, slightly yellow liquid with no haze
Gardner Color: <1
Acidity: <0.001 meq/100 gram sample (ASTM D 1613-91)
GC Purity: 97.4%
Residual Titanium: <0.1 ppm (lower detection limit)
Residual Magnesium: <0.1 ppm (lower detection limit)

Example II

The serial water washing of Example I (step 2) is replaced with the addition of 1.5 grams magnesium acetate. The resultant product is nearly colorless with equal product quality properties and yield as in Example 1.

Example III

The 2-ethylhexanol of Examples I or II is replaced with a mixture of straight and branched chain alcohols (480 grams) with nine to eleven carbons (e.g., Neodol 91 manufactured by Shell Chemical Company). The resultant product quality is comparable to the results of Examples I and II with a product yield of 750 grams. Product purity was slightly lower due to the mixed esters produced from the transesterification of the alkyl groups of the catalyst.

Example IV

The 2-ethylhexanol of Examples I or II is replaced with 432 grams of 3,3,5-trimethyhexanol (also known as isononyl alcohol). The resultant product quality is comparable to the above examples with a product yield of 719 grams. Product purity is slightly lower due to the mixed esters produced from the transesterification of the alkyl groups of the catalyst.

Example V

The 2-ethylhexanol of Examples I or II is replaced with a mixture of straight and branched chain alcohols (516 grams) with eleven carbons (comparable to Newdol 1 manufactured by Shell Chemical or Lial 111 manufactured by EniChem). The resultant product quality is comparable to the above examples with a product yield of 774 grams. Product purity is slightly lower due to the mixed esters produced from the transesterification of the alkyl groups of the catalyst.

Example VI

The 2-ethylhexanol of Examples I or II is replaced with a isodecyl alcohol (comparable to Exxal 10 manufactured by Exxon Chemical) (474 grams). The resultant product quality is comparable to the above examples with a product yield of 764 grams. Product purity is slightly lower due to the mixed esters produced from the transesterification of the alkyl groups of the catalyst.

Example VII

The 2-ethylhexanol of Examples I or II is replaced with isotridecyl alcohol (comparable to Exxal 13 manufactured by Exxon Chemical) (600 grams). The resultant product quality is comparable to the above examples with a product yield of 828 grams. Product purity is slightly lower due to the mixed esters produced from the transesterification of the alkyl groups of the catalyst.

Example VIII

The 2-ethylhexanol of Examples I or II is replaced with n-octanol (comparable to Alfol 8 manufactured by Vista Chemical or Epal 8 manufactured by Albemarle) (390 grams). The resultant product quality is comparable to the above examples with a product yield of 695 grams. Product purity is slightly lower due to the mixed esters produced from the transesterification of the alkyl groups of the catalyst.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A process for the preparation of a dialkyl tetrahalophthalate, comprising;
   a. dissolving a tetrahalophthalic anhydride containing up to about 0.30% residual sulfuric acid, in a $C_1$–$C_{18}$ alkanol, to form a reaction mass;
   b. removing residual sulfuric acid from the reaction mass using a treatment selected from the group consisting of serial water washes, and treatment with a first Group II alkali metal salt of a low number carbon chain organic acid;
   c. removing water from said reaction mass;
   d. esterifying with an alkyl titanate catalyst; and
   e. treating with a second Group II alkali metal salt and water to decolorize and remove residual metal contamination and acidity.

2. The process of claim 1, wherein the tetrahalophthalic anhydride is tetrabromophthalic anhydride.

3. The process of claim 1, wherein the alkanol is selected from the group consisting of 2-ethylhexanol; 3,3,5 trimethylhexanol; and mixtures of $C_{8-15}$ alkanols resultant from Oxo- and/or Ziegler manufacturing processes.

4. The process of claim 1, wherein the first Group II alkali metal salt is a magnesium or calcium salt of a low number carbon chain organic acid.

5. The process of claim 4, wherein the first Group II alkali metal salt is magnesium acetate.

6. The process of claim 4, wherein the first Group II alkali metal salt is utilized at 0.01 to 10 percent of the weight of the reaction mass.

7. The process of claim 1, wherein the alkyl titanate catalyst catalyzes the esterification at temperatures from 180°–210° C.

8. The process of claim 1, wherein the second Group II alkali metal salt is magnesium silicate.

9. The process of claim 8, wherein about 0.1 to 20 weight percent of magnesium silicate is utilized based on the weight of the reaction mass.

10. The process of claim 1, wherein the first Group II alkali metal salt is used an amount stoichiometrically equal to the amount of residual sulfuric acid in the reaction mass.

11. The process of claim 1, wherein the alkyl titanate catalyst contains an alkyl group which is identical to the alkyl group of the alkanol.

12. A process for preparation of a dialkyl tetrahalophthalate by esterification of a tetrahalophthalic anhydride containing up to about 0.30% residual sulfuric acid, with a $C_{1-18}$ alkanol or mixtures thereof to form a reaction mass in the presence of an alkyl titanate catalyst, comprising:

a. prior to the esterification, removing residual sulfuric acid from the tetrahalophthalic anhydride, using a treatment selected from the group consisting of serial water washes, and treatment with a first Group II alkali metal salt of a low number carbon chain acid;

b. removing water from said reaction mass; and c. after esterification, treating the dialkyl tetrahalophthalate with an amount of a second Group II alkali metal salt and an equal amount of water to decolorize and remove residual metal contamination and acidity.

13. The process of claim 12, wherein the first Group II alkali metal salt is a magnesium or calcium salt of a low number carbon chain organic acid.

14. The process of claim 13, wherein the first Group II alkali metal salt is magnesium acetate.

15. The process of claim 12, wherein the alkyl titanate catalyst catalyzes the esterification at temperatures from 180°–210° C.

16. The process of claim 12, wherein the second Group II alkali metal salt is magnesium silicate.

17. The process of claim 12, wherein the alkyl titanate catalyst contains an alkyl group which is identical to the alkyl group of the alkanol.

18. The process of claim 12, wherein the first Group II alkali metal salt is used an amount stoichiometrically equal to the amount of residual sulfuric acid in the reaction mass.

19. The process of claim 1, wherein the reaction temperature for treating with a second Group II alkali metal salt and water to decolorize and remove residual metal contamination and acidity is from approximately 50°–95° C.

20. The process of claim 1, wherein the reaction time for treating with a second Group II alkali metal salt and water to decolorize and remove residual metal contamination and acidity is from approximately 1–4 hours.

* * * * *